(12) United States Patent
Lindström (10) Patent No.: US 7,849,536 B2
(45) Date of Patent: Dec. 14, 2010

(54) UNDERLAY

(75) Inventor: Åsa Lindström, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 161 days.

(21) Appl. No.: 12/086,391

(22) PCT Filed: Dec. 14, 2005

(86) PCT No.: PCT/SE2005/001929

§ 371 (c)(1),
(2), (4) Date: Jun. 12, 2008

(87) PCT Pub. No.: WO2007/069950

PCT Pub. Date: Jun. 21, 2007

(65) Prior Publication Data

US 2009/0169800 A1    Jul. 2, 2009

(51) Int. Cl.
*A61F 13/15* (2006.01)
(52) U.S. Cl. .................. 5/484; 5/486; 5/487; 5/494; 604/385.11; 604/392
(58) Field of Classification Search .............. 5/484, 5/486–488, 494; 604/385.11, 392
See application file for complete search history.

(56) References Cited

U.S. PATENT DOCUMENTS

| | | | | |
|---|---|---|---|---|
| 1,649,958 A | * | 11/1927 | Hoyme | ............ 604/392 |
| 3,765,040 A | * | 10/1973 | Holstein | ............ 5/487 |
| 4,909,802 A | * | 3/1990 | Ahr et al. | ............ 604/385.3 |
| 6,110,157 A | | 8/2000 | Schmidt | |
| 7,159,257 B1 | * | 1/2007 | Struthers | ............ 5/487 |
| 2004/0207239 A1 | | 10/2004 | King | |
| 2005/0028278 A1 | | 2/2005 | Landry | |

FOREIGN PATENT DOCUMENTS

| | | |
|---|---|---|
| CN | 1145216 | 3/1997 |
| EP | 0 218 568 A1 | 4/1987 |
| EP | 1 106 115 A1 | 6/2001 |
| GB | 2 300 806 A | 11/1996 |
| WO | WO 99/01091 A1 | 1/1999 |

OTHER PUBLICATIONS

PCT/ISA/210.
PCT/ISA/237.
An English Translation of the Notification of the First Office Action issued in corresponding Chinese Application No. 200580052227.X dated Oct. 30, 2009.

* cited by examiner

*Primary Examiner*—Michael Trettel
(74) *Attorney, Agent, or Firm*—Buchanan Ingersoll & Rooney PC (57) ABSTRACT

Underlay for single use for protection of e.g. chair cushions, bedclothes or changing tables, having a liquid-receiving coversheet intended to face away from the object requiring protection, a liquid impermeable backsheet intended to face the object requiring protection upon use, wherein the underlay can be attached to the user.

24 Claims, 10 Drawing Sheets

UNDERLAY

FIELD OF INVENTION

The present disclosure concerns an underlay for single use comprising a longitudinal symmetry line, a first longitudinal edge and a second longitudinal edge, a first transverse edge and a second transverse edge. The underlay is intended to protect an object requiring protection such as for example chair cushions, bed clothes or changing table from a user's bodily waste. The underlay comprises a liquid-receiving coversheet intended to face the user and a substantially liquid-impermeable backsheet intended to face away from the user.

TECHNICAL BACKGROUND

Various types of underlays for single use such as chair or bed-protectors are used in hospitals and other care institutions and home-care, so as to prevent urine and/or faecal matter penetrating and fouling bedclothes and mattresses in beds and sitting surfaces on chairs. Upon changing a baby's diaper, it is not uncommon that an underlay is used to protect e.g. the changing table or the surface upon which diapers are changed. An example of an underlay is described in EP 0,218, 568.

One problem connected with the use of an underlay for the protection of various objects requiring protection is that the underlay does not lie still in its intended place and protect the object requiring protection from contamination from urine or faeces from a user. The problem is especially great when the user is very mobile, such as e.g. a child on a changing table or a restless incontinent adult person in a hospital bed.

There is therefore a need for an underlay which does not end up in the wrong place in relation to the user and the object requiring protection when the underlay is used.

OBJECT AND SUMMARY

The present disclosure provides an underlay of the type described in the introduction which substantially avoids the problems which have been associated with the earlier known articles.

An underlay is primarily characterized in that the underlay comprises means for attaching the underlay to a user.

By attaching the underlay to the user in an effective way, the underlay follows the movements of the user, whereby the underlay is always located in a position such that bodily waste ends up on the surface of the underlay.

According to one embodiment, the means for fixing the underlay to the user comprises a belt intended, upon use, to attach the underlay to the user.

According to a second embodiment, the underlay comprises a first weakening, wherein a first narrow strip protruding from the underlay is formed when the underlay is torn apart at the weakening. The strip thereby has a free end, whereby the strip forms a belt intended to attach the underlay to the user.

According to one embodiment, the weakening consists of a perforation.

According to one embodiment the underlay is intended for adult users, whereby the perforation has a length of 60-150 cm, preferably 80-130 cm and even more preferably 90-125 cm.

The underlay may be shaped so that the maximal length of the belt which can be formed when the entire perforation is torn apart can reach around even the broadest user.

According to one embodiment the underlay is intended for infants, whereby the perforation has a length of 30-50 cm, preferably 40-50 cm and even more preferably 40-45 cm.

According to one embodiment, the underlay comprises a separate narrow material piece, wherein said material piece forms a belt. The belt comprises a first end region permanently bonded to the liquid-receiving coversheet or to the substantially liquid-impermeable backsheet. The belt further comprises a free end.

Upon manufacture of the underlay, it is relatively simple to apply a separate belt to in principle any underlay, and one can even imagine manufacturing both traditional underlays and underlays comprising a belt according to this embodiment in the same machine.

One embodiment is characterised in that the underlay is intended for adult users, whereby the belt has a length of 60-150 cm, preferably 80-130 cm and even more preferably 90-125 cm.

One embodiment concerns an underlay intended for infants, whereby the belt has a length of 30-50 cm, preferably 40-50 cm and even more preferably 40-45 cm.

Another embodiment is characterised in that the belt extends substantially at right angles to the symmetry line before use, and according to another embodiment, the belt extends substantially parallel to the symmetry line before use.

According to one embodiment, the free ends of the belt comprise at least one adhesive surface intended to attach to the liquid-receiving coversheet or with the substantially liquid-impermeable backsheet when the underlay is attached to the user. Adhesive attachment of the free ends of the belt to the liquid-receiving coversheet or backsheet of the underlay is a very cheap way of attaching the belt around a user.

According to one embodiment, the liquid-receiving coversheet or the substantially liquid-impermeable backsheet of the underlay comprises at least one surface intended to cooperate with the adhesive surface which is arranged at the free ends of the belt. A surface which is intended to cooperate with the adhesive surface on the belt can be better suited in regard to properties such as e.g. opening forces when the underlay is to be discarded and the connection is to be broken.

One embodiment is characterised in that the free ends of the belt comprise at least one hook and loop fastener and that the liquid-receiving coversheet or liquid-impermeable backsheet of the underlay comprise at least one reception surface intended to cooperate with the hook and loop fastener when the underlay is attached to the user.

Hook and loop fastening of the belt around a user is advantageous as a hook and loop fastening is not sensitive to humidity or skin creams.

One embodiment is characterised in that the belt comprises a first belt half protruding from the underlay and a second belt half protruding from the underlay. Both belt halves thereby have free ends, and whereby the belt halves are intended to be attached to each other in use.

A belt comprising two belt halves is simple to fasten around a user upon attachment of the underlay to the user.

According to one embodiment, the underlay is intended for adult users, whereby each belt half has a length of 40-75 cm, preferably 50-70 cm and even more preferably 50-60 cm.

Another embodiment concerns an underlay intended for infants, wherein each belt half has a length of 20-40 cm, preferably 20-35 cm and even more preferably 25-30 cm.

According to one embodiment, the underlay comprises a second weakening, wherein a second narrow strip protruding from the underlay is formed when the underlay is torn apart at the second weakening. The second strip has a free end, wherein the second strip forms a second belt half, and whereby the first strip forms a first belt half. The belt halves are intended to be attached to one another when the underlay is attached to the user.

One embodiment is characterised in that the second weakening comprises a perforation.

The underlay according to one embodiment comprises a second separate narrow material piece forming a second belt half. The second belt half comprises a first end area which is permanently attached to the liquid-receiving coversheet or to the substantially liquid-impermeable backsheet, and a free end. The first separate narrow material piece forms a first belt half, wherein the belt halves are intended to be attached to one another when the underlay is attached to the user.

One embodiment is characterised in the belt halves extend substantially at right angles to the symmetry line of the underlay before use.

According to one embodiment, the free end of the first belt half comprises at least one adhesive surface intended to be attached to the second belt half, and according to another embodiment, the second belt half comprises at least one surface intended to cooperate with the adhesive surface.

According to another embodiment, the free end of the first belt half comprises at least one hook and loop fastener intended to be attached to the second belt half, and according to one embodiment, the free end of the second belt half comprises at least one surface intended to cooperate with the hook and loop fastener.

One embodiment is characterised in that the belt is arranged in connection with any of the transverse edges of the underlay when the underlay is attached to the user, and in another embodiment, the belt is arranged substantially centrally in the length direction of the underlay when the underlay is attached to the user.

In one embodiment, the underlay is intended to protect at least a part of a mattress. One of the most common areas of use of the underlay is to protect beds, mattresses and bedclothes in care wards where elderly, often incontinent, patients reside.

The underlay according to one embodiment is intended to protect a changing table when changing a baby diaper, and according to another embodiment, the underlay is intended to protect a chair seat, for example on a wheelchair.

According to one embodiment, the underlay is intended for adult users, wherein the belt has a width of 2-15 cm, preferably 4-10 cm and even more preferably 5-8 cm.

One embodiment of the underlay concerns an underlay intended for infants, wherein the belt has a width of 2-15 cm, preferably 3-10 cm and even more preferably 5-6 cm.

According to one embodiment the means for attaching the underlay to the user comprises at least two reception surfaces arranged at a distance from one another. One reception surface is intended to be removably attached to one end area of a narrow belt, and wherein the other reception surface is intended to be removably attached to the opposite end area of the belt.

The embodiment means that a loose belt is used together with the underlay, whereby the belt is attached to the underlay on each side of the user. As the belt is removably attached to the underlay, it can be used many times, for many sequential underlays.

The reception surfaces are—according to one embodiment—symmetrically arranged around the longitudinal symmetry line of the underlay.

One embodiment is characterised in that the means for attaching the underlay to the user comprises a reception surface, wherein the reception surface is intended to be removably attached to the centre portion of a narrow belt. The embodiment means that one end area of the comprises a belt half and the other end area comprises the opposite belt half when a belt is removably attached to the underlay. This belt can also be used for several underlays, as it is removably attached to the underlay.

According to one embodiment, the means for attaching the underlay to the user comprises a reception surface arranged substantially on the longitudinal symmetry line of the underlay, wherein the reception surface is intended to be removably attached to the centre portion of a narrow belt.

One embodiment is characterised in that the reception surfaces are intended to be removably attached to an adhesive surface, and another embodiment is characterised in that the reception surfaces are intended to be removably attached to a hook and loop fastener.

DETAILED DESCRIPTION OF THE PREFERRED EMBODIMENTS

The disclosure concerns an underlay 1 for single use.

The underlay 1 of the aforementioned type has many different uses within institutional care, home care and care of small children who are not yet continent.

The underlay 1 is primarily used in the care of incontinent patients, to protect bedclothes and mattresses, but the protection of chair cushions, wheelchairs or similar is also a frequent occurrence. A changing table, upon which one changes the diapers of infants, is a further example of a surface which is commonly protected with the help of various types of underlay 1.

Figure 1:
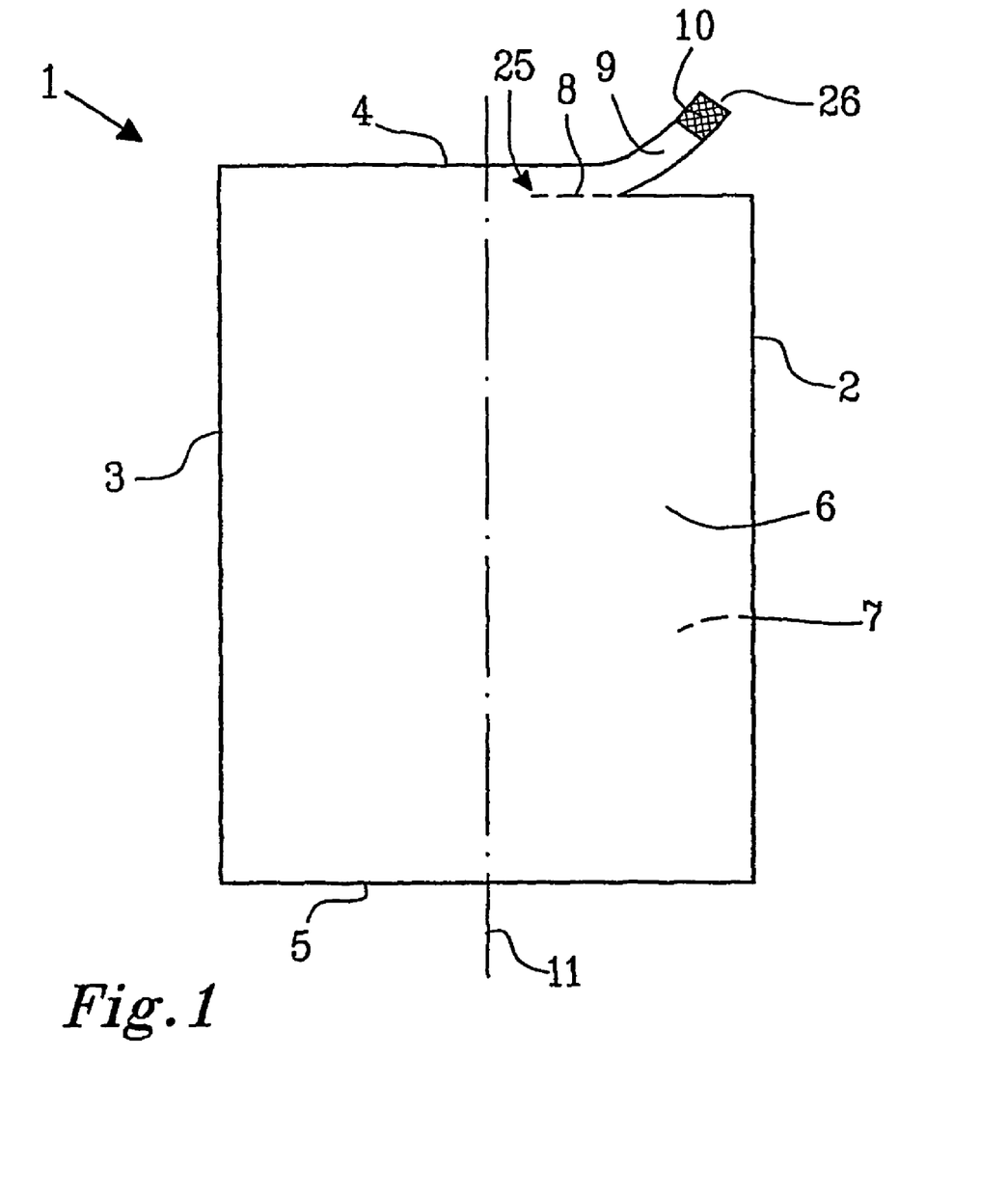
FIG. 1 shows an underlay in accordance with a first embodiment of the invention, from the side which is intended to face away from the object which is to be protected.

FIG. 1 shows the components of an underlay 1. The underlay 1 is primarily intended for the protection of a changing table upon changing a diaper on an infant.

The underlay 1 is substantially rectangular and has two longitudinal edges 2, 3 and two transverse edges 4,5.

The underlay 1 comprises a liquid-receiving coversheet 6, arranged over the surface of the underlay 1 which is intended to face the user when in use. As the underlay does not comprise any specific absorbent body, the liquid-receiving coversheet 6 is a combination sheet having both liquid-accepting properties and certain liquid-absorption properties. The liquid-receiving coversheet 6 according to the described embodiment can comprise whichever material is suitable for the purpose. Examples of commonly-used liquid-receiving coversheets are non-woven textile materials, textile materials, liquid-receiving foam sheets or the like. Liquid-receiving coversheets which are made of continuous thin fibres which extend over the entire underlay is also possible. Laminates comprising two or more of the above-mentioned possible cover materials are also possible, as are covers comprising different materials in different areas of the surface. To ensure a certain absorption ability, the liquid-receiving coversheet 6 comprises absorbent material. Examples of suitable materials are cotton fibres, rayon fibres or similar. One might also consider certain mixtures of cellulose fibres in an absorbent reception sheet. The underlay 1 constructed without a separate absorbent body is primarily intended for situations where one does not expect any large amounts of absorption.

The underlay 1 according to the described embodiments also has a backsheet 7 arranged over the surface of the underlay which, when in use, is intended face the object which the underlay is intended to protect. Normally occurring backsheets 7 on the underlay 1 tend to be liquid impermeable, but other types of backsheet are also be possible. The backsheet 7 can comprise a range of different materials. It is most common that the backsheet 7 is formed of a thin liquid-impermeable plastic film, but it is also possible to use other types of liquid-impermeable materials, such as nonwoven materials which are made liquid impermeable through e.g. a plastic coating, liquid-impermeable foam layer, liquid-impermeable glue, or similar. The backsheet 7 can also be formed of a liquid-impermeable, vapour-permeable material, whereby the underlay 1 has a certain breathability, which makes the underlay more comfortable to use.

In alternative embodiments, the backsheet 7 may be formed of a laminate. Such laminates normally comprise a liquid-impermeable material functioning as a liquid barrier, and a more textile-like material arranged on the side of the underlay 1 which is oriented towards the object requiring protection. Underlays having such a backsheet have higher friction with the object to be protected as compared to e.g. an underlay with a smooth plastic backside, whereby the likelihood that the underlay moves out of position upon use is reduced. The textile-like layer of the laminate is usually formed from a non-woven sheet, but can of course be formed from other textile materials.

To ensure that the underlay 1 remains in place without sliding against the underlay (object requiring protection), underlays 1 also exist with adhesive surfaces and/or high-friction surfaces arranged on suitable parts of the side of the underlay which is intended to face the object to be protected.

The liquid-receiving coversheet 6 and backsheet 7 are attached to each other over the entire area of the coversheet, but in alternative embodiments, can be intermittently attached to each other.

The liquid-receiving coversheet 6 and the backsheet 7 can be attached to one other in a number of different ways. Examples of ways of attaching are gluing, hot-melting or ultrasound welding.

The underlay 1 is primarily characterised in that it has a weakening 25 in the form of a perforation 8 extending substantially at right angles to the longitudinal symmetry line 11 of the underlay 1, whereby a narrow strip is formed when the perforation is activated; i.e. when the underlay 1 is torn apart at the perforation 8. The narrow strip forms a belt 9 intended to encircle a user upon use of the underlay 1. In order to better illustrate the embodiment, the perforation 8 has been torn apart along a short length in FIG. 1.

The perforation 8 extends from the longitudinal edge 2 of the underlay 1 in towards the longitudinal symmetry line 11, substantially parallel with the transverse edge 4 of the underlay 1. The perforation 8 ends before it reaches the longitudinal symmetry line 11 of the underlay 1, whereby the length of the perforation 8 defines the maximal length of the belt 9 which is formed when the entire perforation is torn apart. One can also choose to form a shorter belt 9, by only tearing the perforation 8 apart along a portion of its length. The perforation 8 extends 30-50 cm in from the longitudinal edge 2, preferably 40-50 cm and even more preferably 40-45 cm.

The width of the belt 9 is 2-15 cm, preferably 3-10 cm and even more preferably 3-6 cm.

The belt 9 comprises an adhesive surface 10 arranged on the side of the belt 9 which is intended to face the infant upon use of the underlay 1, whereby the adhesive surface 10 is arranged at the free end 26 of the belt 9. The belt 9 is intended to extend across the trunk of an infant, after which the glue surface 10 is intended to be attached to the liquid-receiving coversheet 6 or backsheet 7 of the underlay 1.

In alternative embodiments, the adhesive surface 10 can be arranged on the side of the belt 9 which is intended to face away from the child upon use of the underlay 1.

It is also possible to arrange a special reception surface for the glue surface on the liquid receiving coversheet 6 or backsheet 7 of the underlay 1. The reception surface is thereby formed of a piece of material specially intended to cooperate with the adhesive surface 10. Examples of a suitable material for the piece of material are a plastic film, or similar.

The glue surface 10 is normally protected before use by a removable protection layer. Commonly occurring protection layers are formed of a paper sheet treated with a release agent or similar. No reception surface or protection layer are shown in FIG. 1.

The underlay 1 can be used without tearing the perforation 8 apart, i.e. exactly like previously-known underlays which do not comprise a belt. If one wishes to fasten the underlay 1 to an infant, one tears the perforation 8 apart and encircles the child with the belt 9. Finally, the free end 26 of the belt 9 is attached to the underlay 1.

Figure 2A:
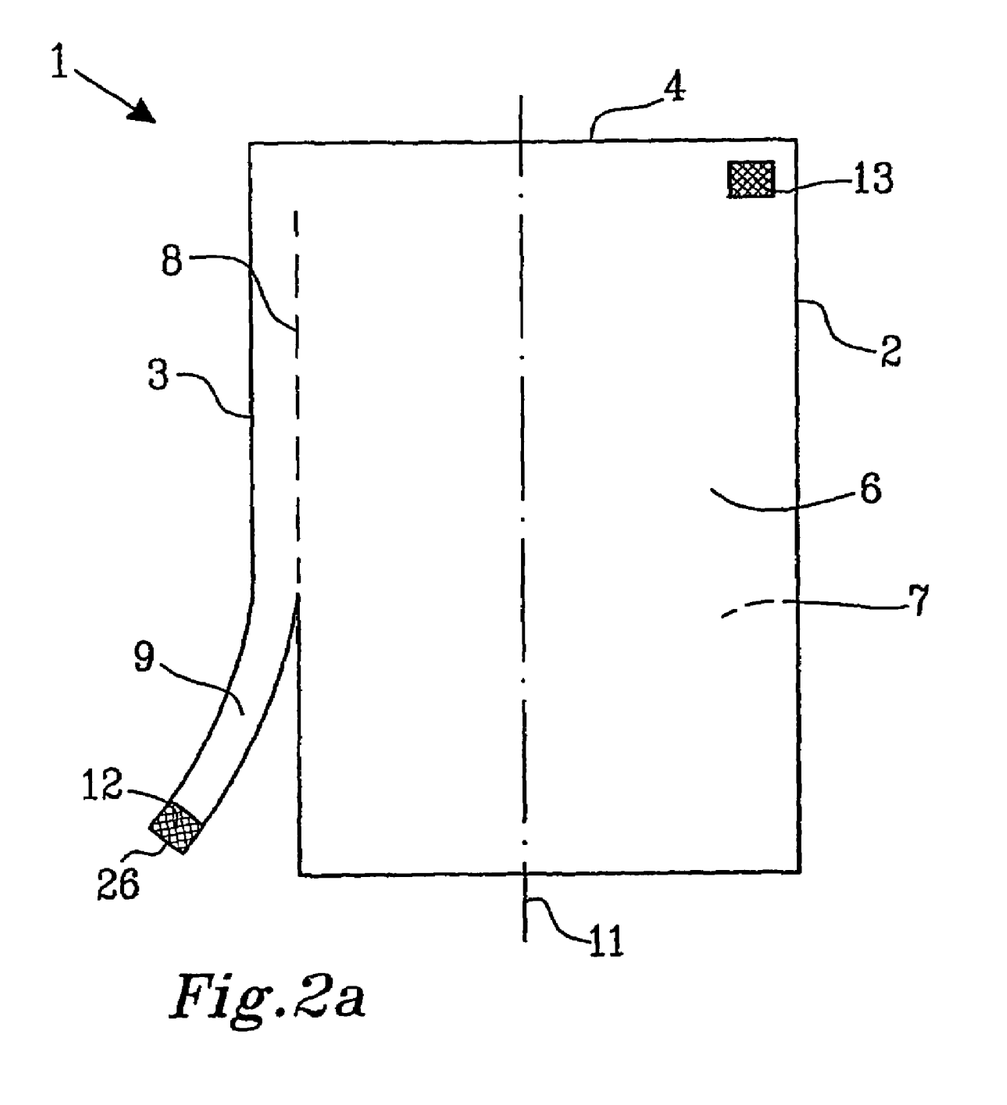
FIG. 2 shows an underlay in accordance with a second embodiment of the invention, from the side which is intended to face away from the object which is to be protected.

FIG. 2 shows an underlay 1 constructed in the same way as the underlay 1 in FIG. 1, but the weakening in the form of a perforation 8 extends along the longitudinal edge 3 of the underlay 1.

The belt 9 which is formed when the perforation 8 is torn apart extends parallel to the longitudinal symmetry line 11 of the underlay 1, whereby it is intended to be folded in against the longitudinal symmetry line 11 in use.

The belt 9 in FIG. 2 comprises a male-type hook and loop fastener 12, a so-called hook surface arranged in connection with the free end 26 of the belt 9.

A reception surface 13 intended to cooperate with the hook and loop fastener 12 is arranged on the underlay 1, at the longitudinal edge 2 which is opposite the belt 9. The reception surface 13 is formed from a female-type hook and loop material, a so-called loop material.

The reception surface 13 is arranged on the liquid-receiving coversheet 6 of the underlay 1, but can also be arranged on the backsheet 7.

In alternative embodiments, it is possible that the female-type hook and loop fastener is arranged at the free end 26 of the belt 9 and that the male-type hook and loop fastener is arranged on the underlay 1 at the longitudinal edge which is opposite the belt 9.

One can also consider embodiments in which the liquid-receiving coversheet 6 or backsheet 7 of the underlay 1 comprises a material which itself is capable of cooperating with the hook and loop fastener 12, whereby no special reception surface for the hook and loop fastener 12 is required.

Figure 2B:
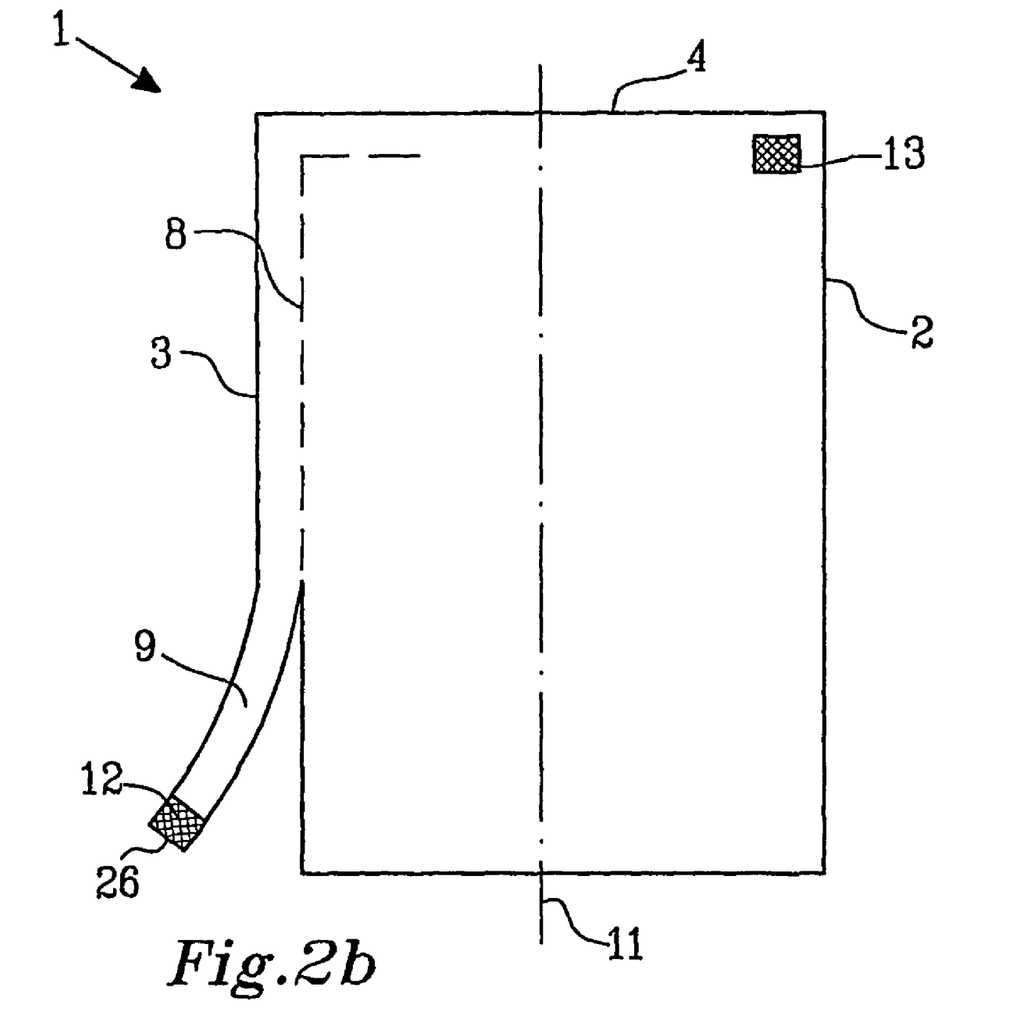
FIG. 2b shows an underlay in accordance with a third embodiment of the invention, from the side which is intended to face away from the object which is to be protected.

FIG. 2b shows an embodiment of the underlay 1 with a weakening in the form of a perforation 8 which extends along the longitudinal edge 3 of the underlay 1 and along the transverse edge 4 of the underlay in towards the longitudinal symmetry line 11. By allowing the perforation 8 to extend both along the longitudinal edge 3 and along the transverse edge 4, one obtains a substantially greater belt length when the perforation 8 is torn apart along its entire length.

The maximal length of the belt 9, i.e. the length which the belt 9 has if the perforation is torn apart along its entire extension is 60-150 cm, preferably 80-130 cm and even more preferably 90-125 cm. The underlay 1 according to this embodiment is especially suited as an underlay for beds, chair cushions or similar intended for adult users.

The belt 9 in FIG. 2b also comprises a male-type hook and loop fastener 12 in connection with the free end 26 of the belt 9.

A female-type reception surface 13 intended to cooperate with the hook and loop fastener 12 is further arranged on the underlay 1 at the longitudinal edge 2 which is opposite the belt 9.

Figure 3:
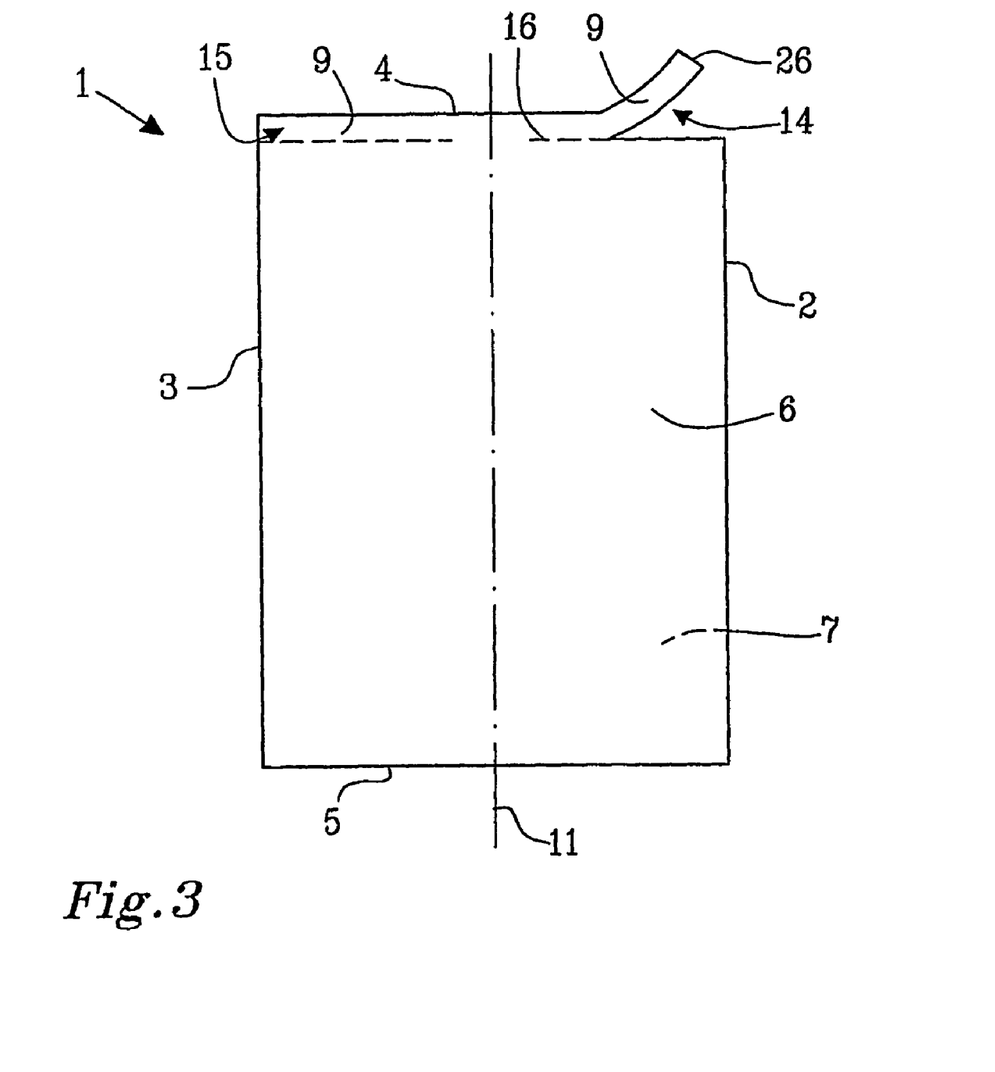
FIG. 3 shows an underlay in accordance with a fourth embodiment of the invention from the side which is intended to face away from the object which is to be protected.

FIG. 3 shows an embodiment of the underlay 1 comprising a belt 9 comprising a first belt half 14 and a second belt half 15. The underlay has the same construction as the underlay 1 in FIGS. 1 and 2, with regard to the liquid-receiving coversheet 6 and the backsheet 7.

The first belt half 14 is formed when the perforation 16 is torn apart and the second belt half 15 is formed when the perforation 17 is torn apart.

Upon use of the underlay 1, the belt halves 14, 15 are connected to each other in a suitable way. For example, one could imagine connecting the belt halves 14, 15 to one another by simply tying them together, after the belt halves 14, 15 have encircled the user.

Alternatively, one of the free ends 26 of the belt halves 14, 15 comprise an adhesive surface or hook and loop fastener intended to cooperate with a purpose-designed reception surface on the opposite belt half 14, 15. The same type of hook and loop fastener, adhesive surface and reception surface as described for the above embodiments are of course also suitable for this embodiment, wherein the hook and loop fastener or the adhesive surface is arranged on one of the belt halves 14, 15 in connection to its free end 26. The reception surfaces are thereby arranged on the other of the belt halves 14, 15 in connection with its free end 26, instead of on the liquid-receiving coversheet 6 or the backsheet 7 of the underlay 1.

In other alternatives, one can consider that the entire belt halves 14, 15 which are intended to receive the adhesive surface or the hook and loop fastener have special properties for receiving the adhesive surface or hook and loop fastener, whereby the possibility for adjustment for different sizes of the user arises.

One can also consider that the belt halves 14, 15 intended to receive the adhesive surface or hook and loop fastener have a number of discrete regions intended to receive the adhesive surface or hook and loop fastener, whereby these discrete regions are arranged along the extension of the belt halves 14, 15.

Naturally, in addition or alternatively, the belt halves 14, 15 which comprise the adhesive surface or hook and loop fastener may comprise a number of discretely-arranged the adhesive surfaces or hook and loop fasteners positioned along the extension of the belt halves 14, 15, whereby adjustment for the size of the user is made possible.

Figure 4:
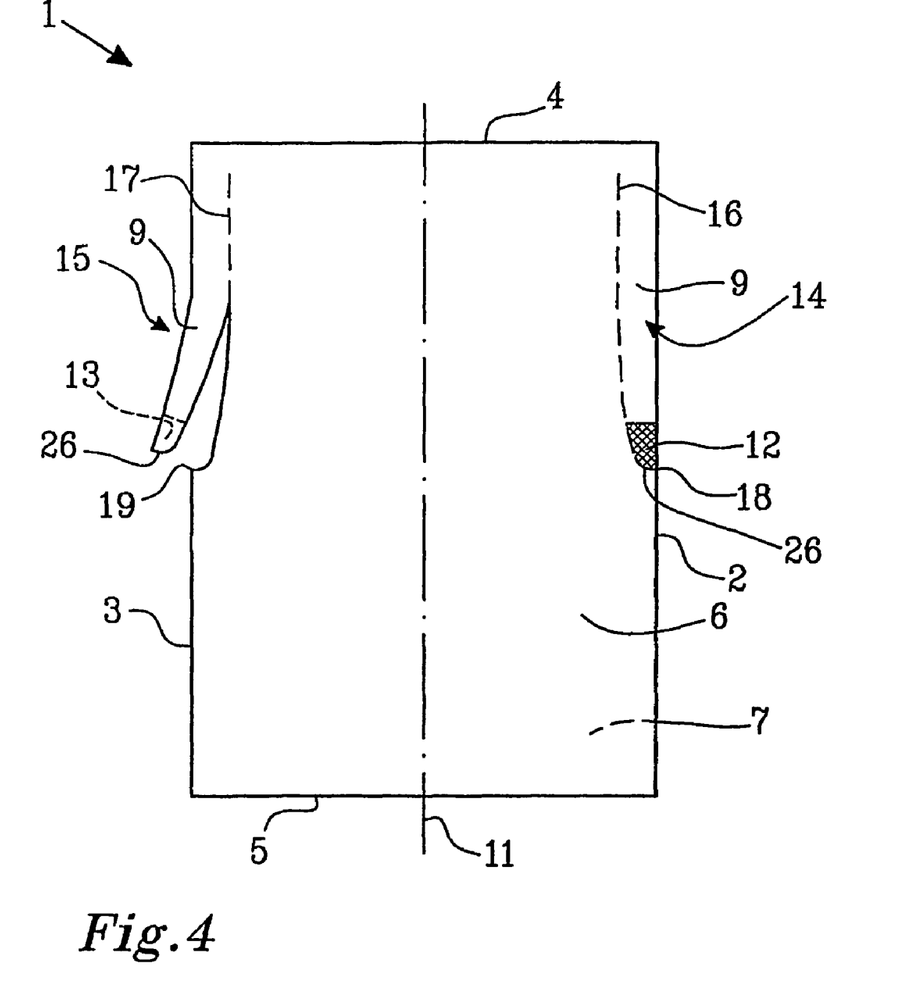
FIG. 4 shows an underlay in accordance with a fifth embodiment of the invention from the side which is intended to face away from the object which is to be protected.

FIG. 4 shows an embodiment of the underlay 1 comprising a belt 9 comprising a first belt half 14 and a second belt half 15. The underlay has the same construction as underlay 1 in FIGS. 1, 2 and 3 with regard to the liquid-receiving coversheet 6 and the backsheet 7.

The underlay 1 has perforations 16, 17 parallel with the longitudinal edges 2, 3 of the underlay 1, whereby a first belt half 14 is formed with perforation 16 is torn apart, and whereby a second belt half 15 is formed when perforation 17 is torn apart.

The perforations 16, 17 extend only along a portion of the longitudinal edges 2, 3 of the underlay 1, whereby the perforations 16, 17 bend out towards the longitudinal edges 2, 3, of the underlay at each free end 26 of the belt halves 14, 15, and end at the longitudinal edges 2, 3 of the underlay 1 at points 18, 19. Points 18, 19 are positioned at a suitable distance from the transverse edge 4 of the underlay 1, so that each belt half constitutes a suitable length to encircle the trunk of a user.

The first belt half 14 comprises a male-type hook and loop fastener 12, a so-called "hook surface" arranged at least in connection with the free end 26 of the first belt half 14, whereby the hook and loop fastener 12 is arranged on the side of the underlay which comprises the liquid-receiving coversheet 6.

A reception surface 13 intended to cooperate with the hook and loop fastener 12 is arranged at the free end 26 of the second belt half 15, whereby the reception surface 13 is arranged on the backsheet 7 of the underlay 1. The reception surface 13 is formed of a female-type hook and loop fastener, a so-called "loop material".

The belt halves 14, 15 which are formed when the perforations 16, 17 are torn apart extend parallel to the longitudinal symmetry line 11 of the underlay 1, whereby each belt half 14, 15 is intended to be bent in towards the symmetry line 11 upon use and to be connected with one another round a user.

In alternative embodiments, one could imagine using adhesive surfaces for connecting the two belt halves 14, 15 to each other. Special reception surfaces intended to cooperate with the adhesive surfaces are thereby also possible.

One can also consider connecting the belt halves 14, 14 to each other by tying them together round the trunk of a user.

Figure 5:
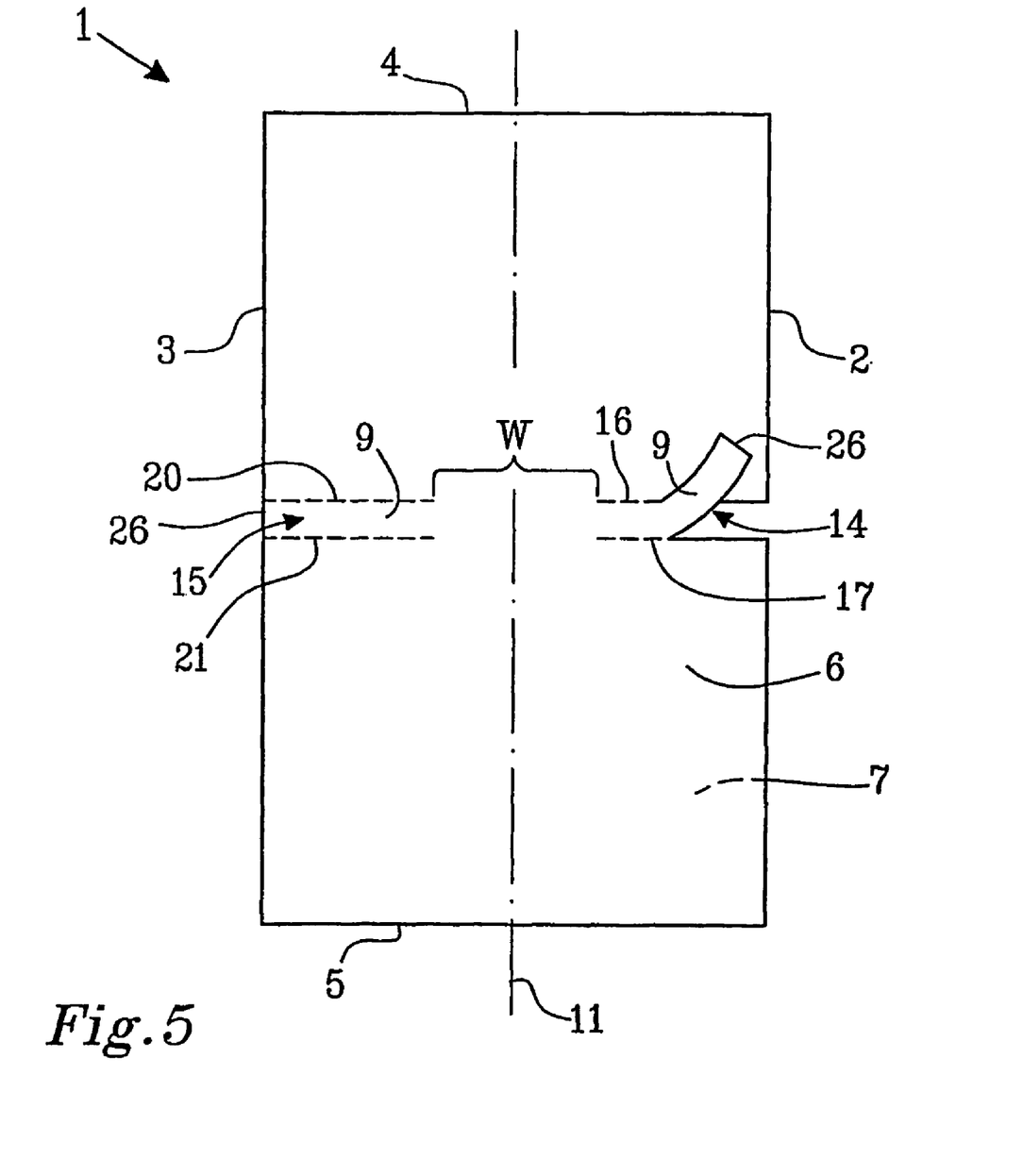
FIG. 5 shows an underlay in accordance with a sixth embodiment of the invention from the side which is intended to face away from the object which is to be protected.

FIG. 5 shows an embodiment of the underlay 1 comprising a belt 9 comprising a first belt half 14 and a second belt half 15.

The underlay has the same construction as the underlay 1 in FIGS. 1, 2, 3 and 4 with regard to the liquid-receiving coversheet 6 and the backsheet 7.

The belt halves 14, 15 are arranged substantially centrally in the longitudinal direction of the underlay 1, whereby the belt halves 14, 15 extend substantially at right angles to the longitudinal symmetry line 11.

The underlay 1 has weakenings in the form of perforations 16, 17, 20, 21, whereby the perforations 16, 17 extend along both longitudinal edges of the first belt half 14 and the perforations 20, 21 extend along both longitudinal edges of the second belt half 15. The first belt half 14 is formed when the perforations 16, 17 are torn apart and the second belt half 15 is formed when the perforations 20, 21 are torn apart.

The belt halves are intended to connect to one another around the trunk of a user, whereby attachment can be made by adhesive attachment, hook and loop attachment or similar. It is also possible to connect the belt halves 14, 15 to each other by tying them together.

Each belt half 14, 15 has a constant width along its entire length, but, in alternative embodiments, can have a variable width along its length. For example, it is suitable to let each belt half 14, 15 be widest at their free ends 26 and to narrow down towards their fixed ends. Such an embodiment means that it is possible to arrange larger connection surfaces at each free end, for e.g. adhesive connection of both belt halves 14, 15 to each other upon use.

The distance W between the two belt halves 14, 15 is dependent on the intended purpose of the underlay 1.

For underlays 1 intended for protection of changing tables when changing diapers of infants, distance W between the belt halves 14, 15 is suitably 12-30 cm, preferably 15-25 cm and even more preferably 15-20 cm.

For underlays 1 intended for incontinent adult users, i.e. for bed protection, chair protection or similar, the distance W between the belt halves 14, 15 is suitably 25-80 cm, preferably 30-60 cm and even more preferably 30-45 cm.

The length of the belt halves is also dependent on the type of use of the underlay 1. For underlays 1 intended for protection of changing tables when changing diapers of infants, the length of each belt half 14, 15 is suitably 20-40 cm, preferably 20-35 cm and even more preferably 25-30 cm.

For underlays 1 intended for incontinent adult users, the length of each belt half 14, 15 is suitably 40-75 cm, preferably 50-70 cm and even more preferably 50-60 cm.

Figure 6:
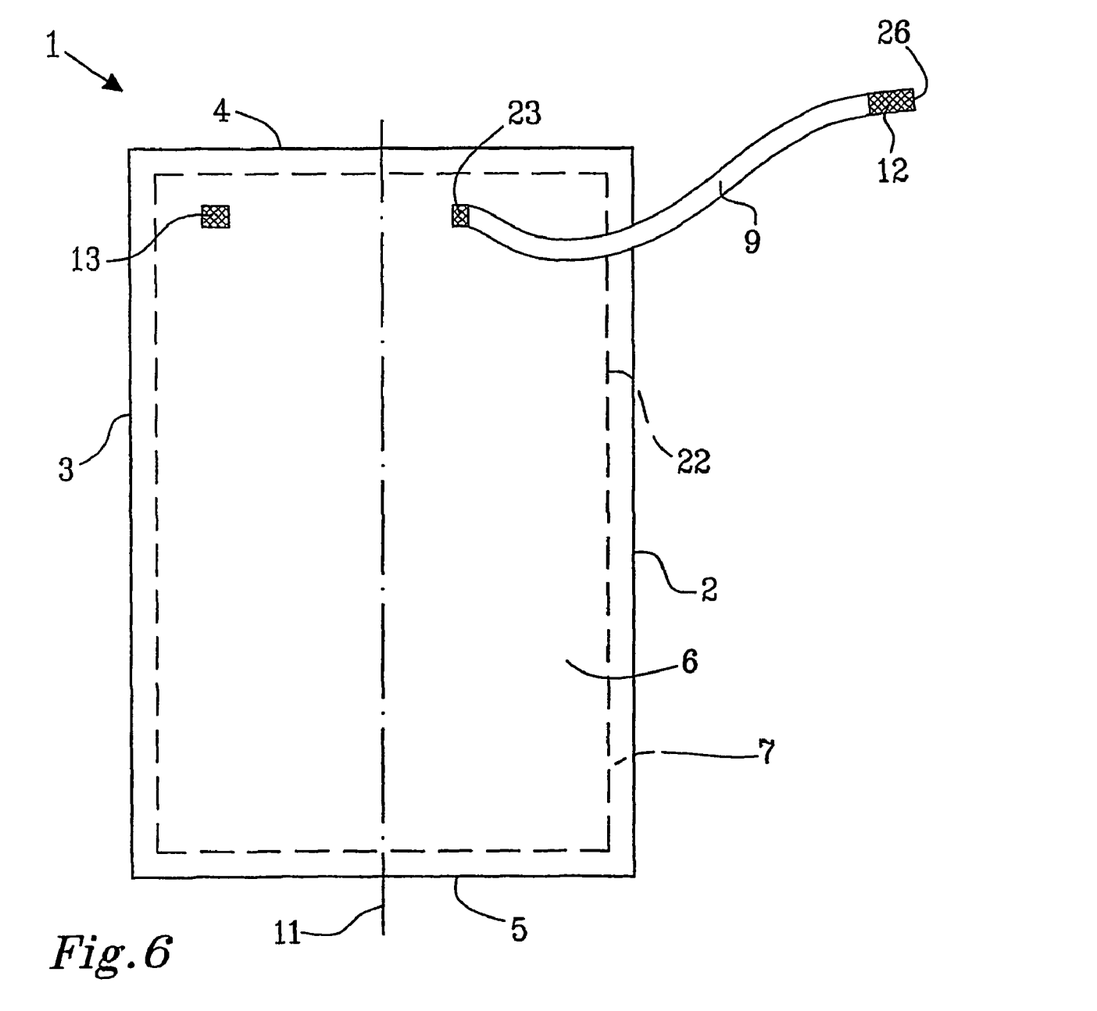
FIG. 6 shows an underlay in accordance with a seventh embodiment of the invention from the side which is intended to face away from the object which is to be protected.

FIG. 6 shows an embodiment of the underlay 1 comprising a separate belt 9. The underlay according to the embodiment described in FIG. 6 differs from the above-described underlays in its construction, in that it comprises a separate absorbent body 22. The underlay 1 is substantially rectangular and has two longitudinal edges 2, 3 and two transverse edges 4, 5.

Just as the previously-described embodiments, the underlay 1 comprises a liquid-receiving coversheet 6 arranged over that surface of the underlay 1 which is intended to face the user upon wearing. The underlay 1 also has a backsheet 7 arranged over that surface of the underlay 1 which is intended to face the object which the underlay is meant to protect when in use.

The basic construction of the underlay differs primarily from the above-described underlays in that it comprises an absorbent body 22 enclosed between the liquid-receiving coversheet 6 and the backsheet 7, whereby it is intended for uses in which one can expect large amounts of liquid to be absorbed.

As the underlay 1 comprises a separate absorbent body 22, one of the primary functions of the liquid-receiving coversheet 6 is to allow liquid through, whereby the absorbent properties of the liquid-receiving coversheet 6 are of no, or minor, importance.

Examples of commonly-occurring materials in the liquid-receiving coversheet 6 are the same types of materials as described above. However, there is no requirement to create absorption properties in the liquid-receiving coversheet 6 through any absorbent material. For the underlay 1 according to this embodiment, it is also conceivable that the liquid-receiving coversheet 6 is formed from a plastic net or a perforated plastic film, in which absorbent properties are completely absent.

An underlay 1 comprising absorbent bodies 22 having especially high strength and wear resistance can even function without any extra liquid-receiving coversheet being required on that side of the underlay 1 which faces the user upon use.

The liquid-receiving coversheet 6 and backsheet 7 of the underlay 1 extend outside the absorbent body 22 along the entire circumference of the absorbent body 22, whereby the coversheet 6 and backsheet 7 are attached to one another outside the absorbent body 22 along the entire circumference of the absorbent body 22. The liquid-receiving coversheet 6 and backsheet 7 can be attached to each other in a number of different ways. Examples of ways of attaching are gluing, heat melting, ultrasound welding or similar.

The underlay 1 further comprises a separate belt 9 permanently attached to the liquid-receiving coversheet 6. The permanent attachment 23 can take place through gluing, heat melting, ultrasound welding or similar. Alternatively, one can consider permanently attaching the belt 9 to the backsheet 7 of the underlay 1.

The belt 9 makes a substantially right angle with the longitudinal symmetry line 11 of the underlay 1.

In alternative embodiments, it is possible that the belt 9 makes another angle with the longitudinal symmetry line 11.

As the belt 9 is formed of a separate piece of material, the length of the belt 9 can be selected independently of the dimensions of the underlay 1.

For underlays 1 intended for protection of changing tables when changing diapers of infants, the length of the belt 9 is 30-50 cm, preferably 40-50 cm and even more preferably 40-45 cm.

The width of the belt 9 is 2-15 cm, preferably 3-10 cm and even more preferably 5-6 cm, for underlays 1 intended for infants.

For underlays 1 intended for incontinent adult users, the length of the belt 9 is suitably 60-150 cm, preferably 80-130 cm and even more preferably 90-125 cm.

The width of the belt 9 is 2-15 centimetres, preferably 4-10 centimetres and even more preferably 5-8 centimetres when the underlay 9 is intended for adult users.

The belt 9 is preferably formed of a laminate comprising a support material and a soft nonwoven material. The support material is thereby arranged on the side of the belt which, in use, is intended to face away from the user and the soft nonwoven material on the belt's opposite side, i.e. against the user. A suitable nonwoven material can be a spunbond nonwoven comprising polypropylene fibres and/or polyethylene fibres. Alternatively, it is possible to use a carded, thermobonded nonwoven which can also comprise polypropylene fibres and/or polyethylene fibres.

A plastic material or a suitable nonwoven material is possible as the support material.

In alternative embodiments, it is possible that the belt has elastic properties.

The free ends 26 of the belt 9 have a male-type hook and loop fastener 12, whereby the hook and loop fastener 12 is arranged on that side of the belt 9 which is intended to face the user when in use.

A special reception surface 13 of the female-type, preferably consisting of a material comprising closed loops, is arranged on the liquid-receiving coversheet 6 of the underlay 1. The reception surface 13 is placed on the underlay 1 in such a way that it can be attached to the hook and loop fastener 12 of the belt 9 when the belt 9 encircles a user who lies or sits on the underlay 1. The attachment between the hook and loop fastener 12 and the reception surface 13 can be opened and reclosed, whereby the belt can be repositioned when the user e.g. changes their sitting or lying position.

Naturally, instead of hook and loop fastening of the belt 9 around the user, one can consider using adhesive fastening as described above.

One can also conceive arranging the reception surface 13 on the backsheet 7 of the underlay 1.

Figure 6B:
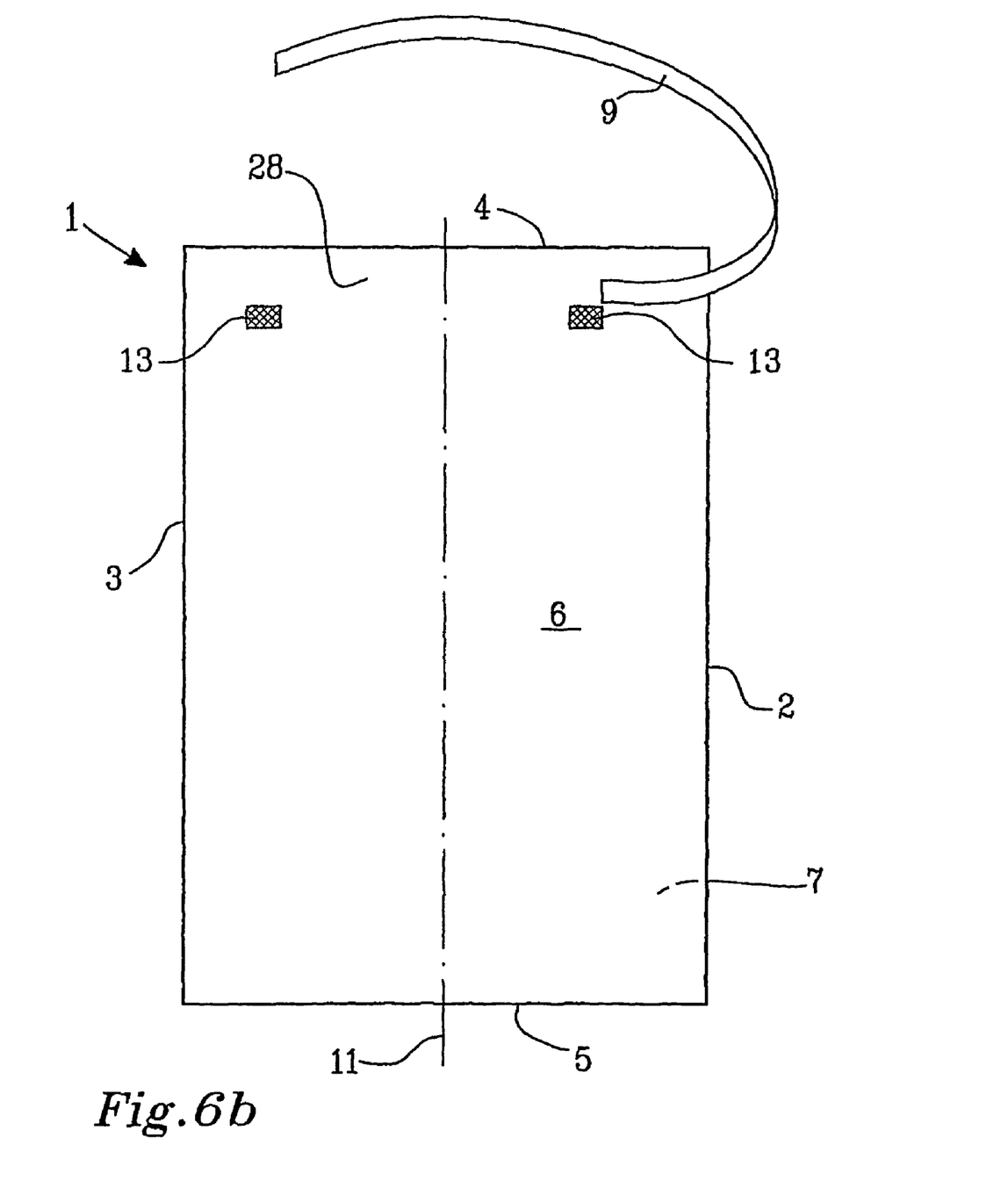
FIG. 6b shows an underlay in accordance with an eighth embodiment of the invention from the side which is intended to face away from the object which is to be protected.

FIG. 6*b* shows a substantially rectangular underlay 1 having two longitudinal edges 2, 3 and two transverse edges 4, 5.

The underlay 1 comprises a liquid-receiving coversheet 6 arranged over that surface of the underlay 1, which is intended to face the user upon wearing, and a backsheet 7.

The underlay is distinguished in that a belt 9 (also shown in FIG. 6*b*) can be affixed to the underlay 1. The belt 9 is thereby removably connectable to the underlay 1, whereby the same belt can be used many times.

The underlay 1 comprises at least two reception surfaces 13, wherein the reception surfaces 13 are arranged symmetrically on each side of the longitudinal symmetry line 11 of the underlay 1.

The reception surfaces 13 are arranged on the liquid-receiving coversheet 6 at one end area 28 of the underlay.

In alternative embodiments, it is possible to arrange the reception surfaces 13 on the backsheet 7 of the underlay 1. One can also consider providing the underlay 1 with a plurality of reception surfaces 13 arranged at varying distances from the longitudinal symmetry line 11 of the underlay 1, whereby one can adjust the belt 9 to users of different sizes.

In other alternative embodiments, one can consider arranging the reception surfaces 13 more centrally on the underlay 1 in the longitudinal direction of the underlay 1.

The reception surfaces 13 are formed of hook and loop fasteners, preferably of the female-type, i.e. surfaces which are formed of a material comprising loops. In alternative embodiments, one can also consider reception surfaces 13 of the male-type comprising hooks.

In other alternative embodiments, the liquid-receiving coversheet 6 is arranged such that it functions as reception material for the male-type hook and loop fasteners, whereby these can be affixed to the underlay 1 at any desired position on the underlay 1.

The removable belt 9 comprises hook and loop fasteners specially designed to cooperate with the hook and loop fasteners which are arranged on the underlay, whereby at least both ends of the belt 9 are provided with such hook and loop fasteners.

Upon use of the underlay 1, the underlay 1 is placed under the user, after which, one attaches the belt 9 on both sides of the user.

Figure 7:
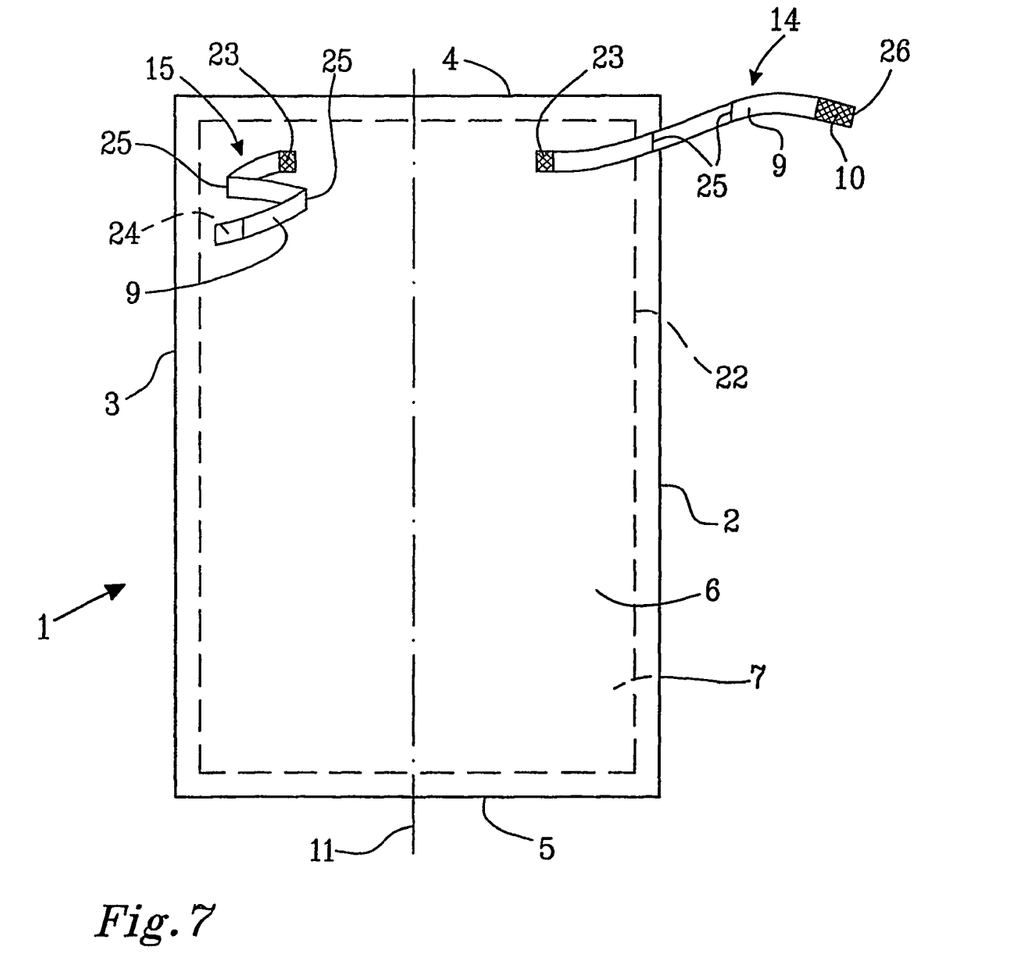
FIG. 7 shows an underlay in accordance with a ninth embodiment of the invention from the side which is intended to face away from the object which is to be protected.

FIG. 7 shows an embodiment of the underlay 1 comprising a separate belt 9 comprising a first belt half 14 and a second belt half 15.

Precisely as for the underlay described in connection with FIG. 6 above, the underlay comprises an absorbent body 22 enclosed between a liquid-receiving coversheet 6 and a backsheet 7.

Each belt half 14, 15 comprises a separate narrow material strip, whereby each belt half 14, 15 is permanently attached to the liquid-receiving coversheet 6 of the underlay 1. The attachment 23 can be arranged in the same way as the corresponding attachment 23 for the belt 9 as described in connection with FIG. 6 above.

In alternative embodiments, it is possible that each belt half 14, 15 is attached to the backsheet 7 of the underlay 1.

In other alternative embodiments, it is possible that the belt 9 is formed of a narrow material strip. The central section of the material strip is thereby attached to the liquid-receiving coversheet 6 of the underlay 1, whereby one end section of the material strip forms the first belt half 14 and the other end section of forms the second belt half 15.

The first belt half 14 comprises an adhesive surface 10 at its free end 26. The second belt half 15 comprises a special reception surface 24 intended to cooperate with the adhesive surface 10. The reception surface 24 is arranged on the second belt half 15 on the side of the second belt half 15 which faces away from the user when the belt 15 encircles the user. By placing the reception surface 24 in this way, one does not need to twist the belt upon use, whereby the belt 9 lies against the user in a comfortable way.

Alternatively, one can consider attaching the belt halves 14, 15 to one another by simply tying them together after having encircled the waist of the user with the belt halves 14, 15.

It is also possible to connect the belt 9 around the user via hook and loop fasteners, whereby it is suitable to provide the side of the belt which faces outwards in use with a material to which a male-type hook and loop fastener can attach.

A button hole in one belt half 14, 15 and a button in the other belt half 14, 15 is also a possible alternative arrangement for fastening the belt 9 around a user.

Upon manufacturing of an underlay 1 according to this embodiment, the two belt halves 14, 15 have been Z-folded against the liquid-receiving coversheet 6, and they have then been fastened in this Z-configuration through easily-broken glue attachments connected to the two fold positions 25. The second belt half 15 in FIG. 7 shows the belt halves when the Z-fold is being folded out, wherein the easily-broken glue attachments have just been broken.

Alternatively, one might conceive other ways of folding, so as to manage the belt halves 14, 15 in a more simple way before use.

Figure 7B:
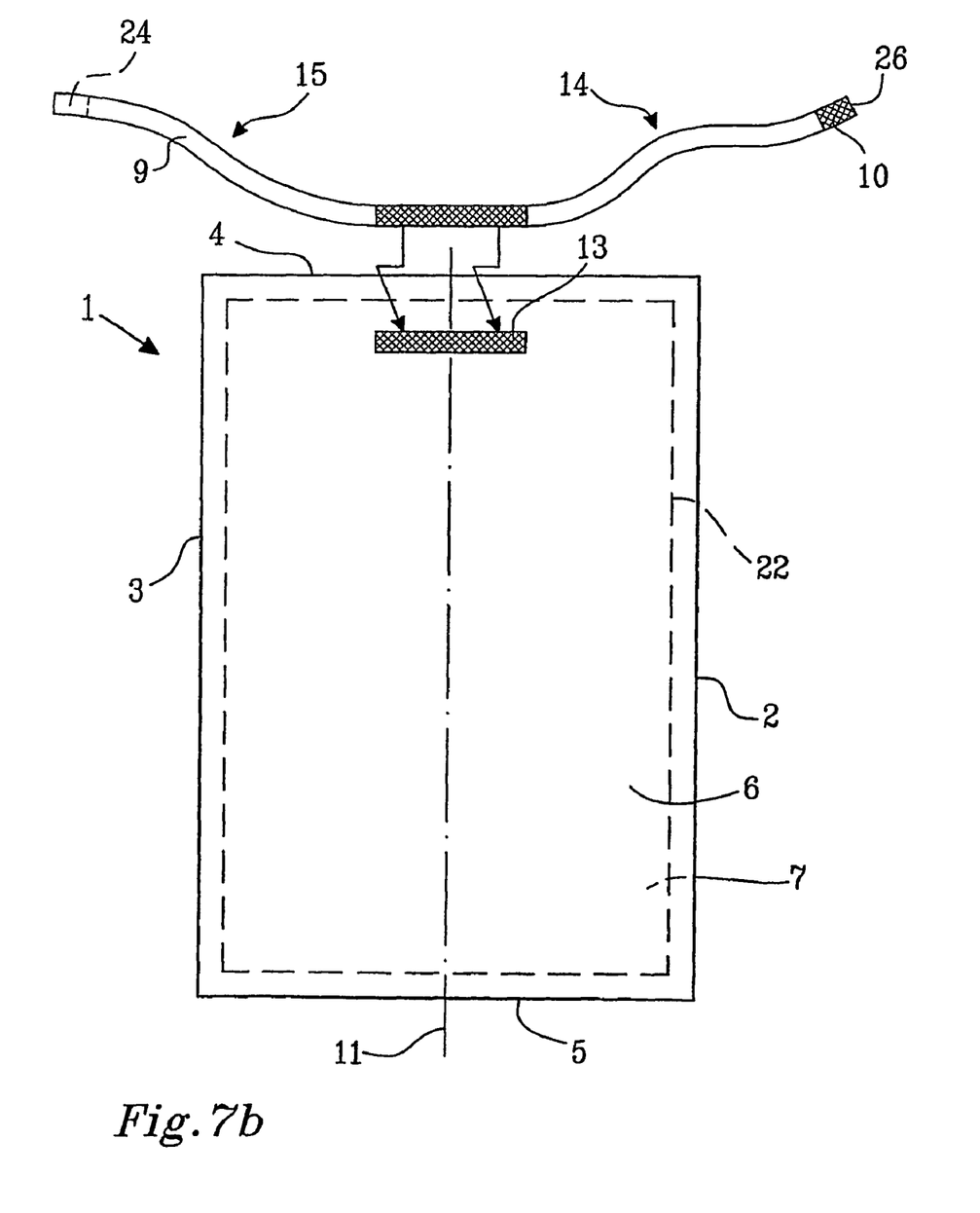
FIG. 7b shows an underlay in accordance with a tenth embodiment of the invention from the side which is intended to face away from the object which is to be protected.

FIG. 7*b* shows an embodiment of the underlay 1 comprising an absorbent body 22 enclosed between a liquid-receiving coversheet 6 and a backsheet 7.

The underlay 1 has a narrow reception surface 13 extending parallel to the transverse edge 4. The reception surface 13 is centred about the longitudinal centre line 11 of the underlay 1 and is intended to be removably attached to a removable belt 9. The reception surface 13 is intended to be attached to the middle section of the belt 9, whereby one end section of the belt 9 forms a first belt half 14 and the other end section forms the second belt half 15 of the belt 9 upon use of the underlay 1 together with the belt 9.

The reception surface 13 is formed from a hook and loop fastening, preferably of the female-type. In alternative embodiments, a reception surface 13 of the male-type comprising hooks is also possible.

In alternative embodiments, the liquid-receiving coversheet 6 is formed so that it functions as a reception material for the male-type hook and loop fastener, whereby no specially-arranged reception surface is required.

The middle section of the removable belt 9 comprises a hook and loop fastener specially designed to cooperate with the reception surface 13 which is arranged on the underlay 1.

In other alternative embodiments, it is possible that the underlay 1 comprises a reception surface 13 specially suited for attachment of an adhesive surface, whereby the central section of the belt 9 comprises an adhesive surface.

When using the underlay 1 together with the belt 9, it is suitable to attach the belt 9 to the underlay, after which one places the underlay 1 on the object to be protected. The underlay 1 is thereafter used in the same way as an underlay 1 which has a permanently fixed belt 9. Alternatively, it is possible that the belt 9 is attached to the user in a first step, after which, the underlay 1 is attached to the belt 9.

The first belt half 14 comprises an adhesive surface 10 at its free end 26 and the second belt half 15 comprises a special reception surface 24 intended to cooperate with the adhesive surface 10, whereby the adhesive surface 10 and the reception surface 24 are attached to one another when the underlay 1 is attached to a user.

Alternatively, the belt halves 14, 15 can comprise hook and loop elements for attachment of the belt to a user.

In an alternative embodiment, it is conceivable that each belt half 14, 15 is comprised of a separate narrow piece of material, whereby each belt half 14, 15 it removably connected to the underlay 1 upon use. For such an embodiment, it is suitable that the underlay 1 has two reception surfaces arranged centrally in relation to the longitudinal symmetry line 11 of the underlay 1.

All of the embodiments described above may also be combined with each other.

Furthermore, the invention is not limited to the above-named embodiments, but can naturally be adapted for other embodiments within the scope of the following claims.

The invention claimed is:

1. A single use underlay for protecting an object requiring protection from a user's bodily waste, said underlay comprising:
    a longitudinal symmetry line, a first longitudinal edge and a second longitudinal edge, first transverse edge and a second transverse edge, a liquid-receiving coversheet intended to face the user and a substantially liquid-impermeable backsheet intended to face away from the user,
    an attachment assembly provided on the underlay to attach the underlay to the user so that the underlay will follow the movements of the user, wherein the attachment assembly comprises a belt adapted, upon use, to attach the underlay to the user, and
    a first weakening, wherein a first narrow strip protruding from the underlay is formed when the underlay is torn apart at the first weakening, the strip has a free end and the strip forms the belt adapted to attach the underlay to the user, and the underlay comprises one single belt.

2. The underlay according to claim 1, wherein the first weakening is comprised of a perforation.

3. The underlay according to claim 2, wherein the underlay is adapted for adult users, and the perforation has a length of 60-150 cm.

4. The underlay according to claim 2, wherein the underlay is adapted for infants, and the perforation has a length of 30-50 cm.

5. The underlay according to claim 1, wherein the belt extends substantially at right angles to the symmetry line before use.

6. The underlay according to claim 1, wherein the belt extends substantially parallel to the symmetry line before use.

7. The underlay according to claim 1, wherein the free end of the belt comprises at least one adhesive surface adapted to attach to the liquid-receiving coversheet or to the substantially liquid-impermeable backsheet when the underlay is attached to the user.

8. The underlay according to claim 7, wherein the liquid-receiving coversheet or substantially liquid-impermeable backsheet of the underlay comprises at least one surface adapted to cooperate with the adhesive surface arranged at the free end of the belt.

9. The underlay according to claim 1, wherein the free end of the belt comprises at least one hook and loop fastener and the liquid-receiving coversheet or liquid-impermeable backsheet of the underlay comprises at least one reception surface adapted to cooperate with the hook and loop fastener when the underlay is attached to the user.

10. The underlay according to claim 1, wherein the belt is arranged in connection with any of the transverse edges of the underlay when the underlay is attached to the user.

11. The underlay according to claim 1, wherein the underlay is adapted to protect at least a part of a mattress.

12. The underlay according to claim 1, wherein the underlay is adapted to protect a changing table when changing a baby diaper.

13. The underlay according to claim 1, wherein the underlay is adapted to protect a chair seat.

14. The underlay according to claim 1, wherein the underlay is adapted for adult users, and the belt has a width of 2-15 cm.

15. The underlay according to claim 1, wherein the underlay is adapted for infants, and the belt has a width of 2-15 cm.

16. A single use underlay for protecting an object requiring protection from a user's bodily waste, said underlay comprising:
    a longitudinal symmetry line, a first longitudinal edge and a second longitudinal edge, first transverse edge and a second transverse edge, a liquid-receiving coversheet intended to face the user and a substantially liquid-impermeable backsheet intended to face away from the user,
    an attachment assembly provided on the underlay to attach the underlay to the user so that the underlay will follow the movements of the user, wherein the attachment assembly comprises a belt adapted, upon use, to attach the underlay to the user, and
    a first separate narrow material piece forming the belt, wherein the belt comprises a first end region permanently bonded to the liquid-receiving coversheet or to the substantially liquid-impermeable backsheet, and wherein the belt comprises a free end,
    wherein the underlay either is adapted for adult users, and the belt has a length of 60-150 cm, or the underlay is adapted for infants, and the belt has a length of 60-150 cm.

17. The underlay according to claim 16, further comprising: a second separate narrow material piece forming a second belt half, wherein the second belt half comprises a first end area which is permanently attached to the liquid-receiving coversheet or to the substantially liquid-impermeable backsheet, wherein the second belt half comprises a free end and wherein the first separate narrow material piece forms a first belt half, wherein the belt halves are adapted to be attached to one another when the underlay is attached to the user.

18. A single use underlay for protecting an object requiring protection from a user's bodily waste, said underlay comprising:
    a longitudinal symmetry line, a first longitudinal edge and a second longitudinal edge, first transverse edge and a second transverse edge, a liquid-receiving coversheet intended to face the user and a substantially liquid-impermeable backsheet intended to face away from the user, and
    an attachment assembly provided on the underlay to attach the underlay to the user so that the underlay will follow the movements of the user, wherein the attachment assembly comprises a belt adapted, upon use, to attach the underlay to the user, wherein the belt is arranged substantially centrally in the length direction of the underlay so that the belt extends from a longitudinal midpoint of the underlay and in a transverse direction toward the longitudinal symmetry line.

19. A single use underlay for protecting an object requiring protection from a user's bodily waste, said underlay comprising:
- a longitudinal symmetry line, a first longitudinal edge and a second longitudinal edge, first transverse edge and a second transverse edge, a liquid-receiving coversheet intended to face the user and a substantially liquid-impermeable backsheet intended to face away from the user, and
- an attachment assembly provided on the underlay to attach the underlay to the user so that the underlay will follow the movements of the user,
- wherein the attachment assembly for attaching the underlay to the user comprises at least two reception surfaces arranged at a distance from one another on the underlay, wherein one reception surface is adapted to be removably attached to one end area of a narrow belt, and wherein the other reception surface is adapted to be removably attached to the opposite end area of the belt.

20. The underlay according to claim 19, wherein the reception surfaces are symmetrically arranged around the longitudinal symmetry line of the underlay.

21. The underlay according to claim 19, wherein the reception surfaces are adapted to be removably attached to an adhesive surface.

22. The underlay according to claim 19, wherein the reception surfaces are adapted to be removably attached to a surface of a hook and loop fastener.

23. A single use underlay for protecting an object requiring protection from a user's bodily waste, said underlay comprising:
- a longitudinal symmetry line, a first longitudinal edge and a second longitudinal edge, first transverse edge and a second transverse edge, a liquid-receiving coversheet intended to face the user and a substantially liquid-impermeable backsheet intended to face away from the user, and
- an attachment assembly provided on the underlay to attach the underlay to the user so that the underlay will follow the movements of the user,
- wherein the attachment assembly comprises a reception surface, wherein the reception surface is adapted to be removably attached to the centre portion of a narrow belt.

24. The underlay according to claim 23, wherein the attachment assembly comprises a reception surface arranged substantially on the longitudinal symmetry line of the underlay.

* * * * *